United States Patent
Lohmann et al.

[11] 4,425,361
[45] Jan. 10, 1984

[54] FORMAMIDO-CARBAMATES AND THEIR USE FOR COMBATING PESTS

[75] Inventors: Dieter Lohmann, Münchenstein; Christian d'Hondt, Riehen; Guenter Rist, Arlesheim, all of Switzerland

[73] Assignee: Ciba-Geigy Corporation, Ardsley, N.Y.

[21] Appl. No.: 322,488

[22] Filed: Nov. 18, 1981

[30] Foreign Application Priority Data

Nov. 27, 1980 [CH] Switzerland .......................... 8807/80
Sep. 25, 1981 [CH] Switzerland .......................... 6204/81

[51] Int. Cl.³ .................. A01N 37/10; C07C 125/065
[52] U.S. Cl. ....................................... 424/309; 560/24; 560/30; 560/31; 560/32; 560/33
[58] Field of Search ....................... 560/32, 31, 30, 24, 560/33; 424/309

[56] References Cited

U.S. PATENT DOCUMENTS 3,935,250  1/1976  Pissiotas .......................... 560/32 X
3,939,274  2/1976  Franke et al. ................... 424/309 X
3,941,829  3/1976  Pissiotas .......................... 560/31
3,962,305  6/1976  Pallos .............................. 560/30 X
4,069,344  1/1978  Karrer ............................. 424/309 X Primary Examiner—Bernard Helfin
Attorney, Agent, or Firm—Frederick H. Rabin; Bruce M. Collins

[57] ABSTRACT

Formamido-carbamates of the formula

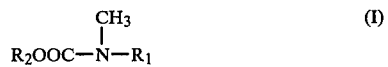

(I)

wherein
$R_1$ is

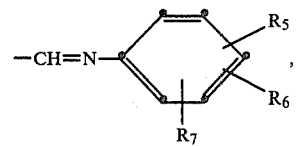

$R_2$ is

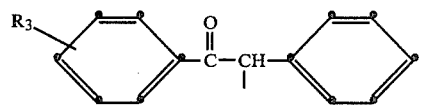

or $R_4$—$CH_2$—$CH_2$—,
$R_3$ is hydrogen,

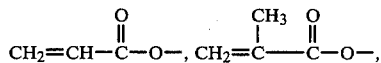

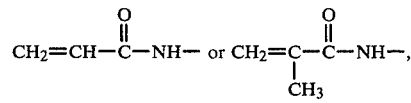

$R_4$ is

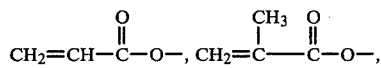

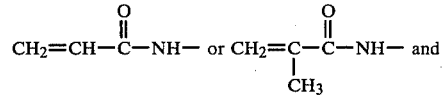
and $R_5$, $R_6$ and $R_7$ independently of one another are each hydrogen, halogen or $C_1$–$C_4$-alkyl, processes for producing them and their use for combating pests are described.

13 Claims, No Drawings

FORMAMIDO-CARBAMATES AND THEIR USE FOR COMBATING PESTS

The present invention relates to formamido-carbamates, to processes for producing them, and to their use for combating pests.

The formamido-carbamates have the formula

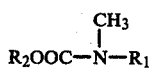

wherein
$R_1$ is

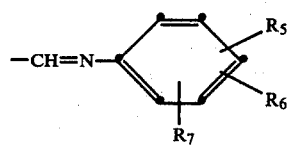

$R_2$ is

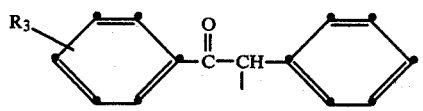

or $R_4$—$CH_2CH_2$—,
$R_3$ is hydrogen,

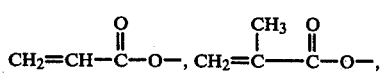

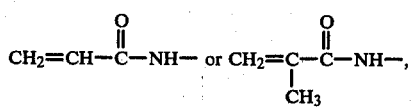

$R_4$ is

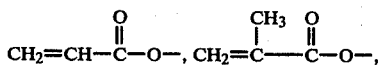

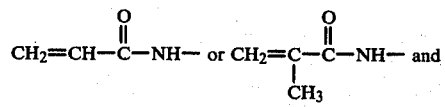

$R_5$, $R_6$ and $R_7$ independently of one another are each hydrogen, halogen or $C_1$–$C_4$-alkyl.

By halogen is meant here fluorine, chlorine, bromine or iodine, especially however chlorine or bromine. The alkyl groups denoted by $R_5$, $R_6$ and $R_7$ are: methyl, ethyl, propyl, isopropyl or n-, i-, sec- and tert-butyl.

Preferred compounds of the formula I are those wherein
$R_1$ is

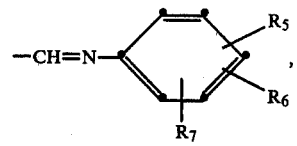

$R_2$ is

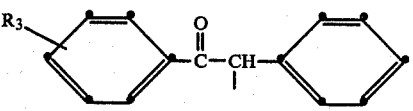

or $R_4$—$CH_2$—$CH_2$—,
$R_3$ is hydrogen or

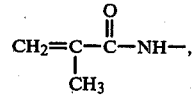

$R_4$ is

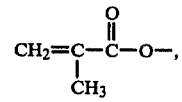

$R_5$ is methyl, chlorine or bromine, and
$R_6$ and $R_7$ are each hydrogen, methyl, chlorine or bromine.

The compounds of the formula I can be produced by methods known per se, for example as follows:

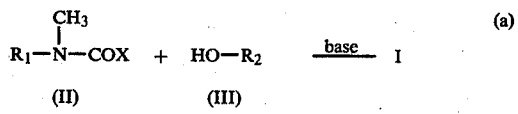 (a)

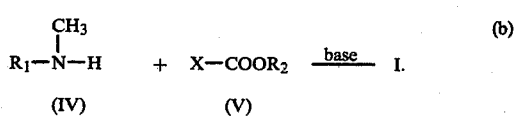 (b)

In the formulae II to V, the symbols $R_1$ and $R_2$ have the meanings defined under the formula I, and X is a halogen atom, particularly a chlorine atom.

The processes are performed at a reaction temperature of between $-50°$ C. and $+130°$ C., preferably between $-10°$ C. and $+100°$ C., under normal or slightly elevated pressure, and in the presence of a base and optionally of a solvent or diluent inert to the reactants.

Suitable bases for the processes of the invention are in particular: tertiary amines, such as trialkylamines, pyridines and dialkylanilines, and also hydroxides, oxides, carbonates and bicarbonates of alkali metals and alkaline-earth metals.

Suitable solvents and diluents are for example: ethers and ethereal compounds, such as diethyl ether, di-isopropyl ether, dioxane, tetrahydrofuran, aliphatic and aromatic hydrocarbons, especially chloroform, benzene, chlorobenzene, toluene and xylenes; ketones, such as acetone, methyl ethyl ketone and cyclohexanone; dimethyl formamide and nitriles, such as acetonitrile.

The starting materials of the formulae II to V are known, or can be produced by methods analogous to known methods.

The compounds of the formula I are suitable for combating pests on animals and plants.

The compounds of the formula I are especially suitable for combating insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and phytopathogenic mites and ticks of the order Acarina.

Compounds of the formula I are suitable in particular for combating insects that damage plants, especially insects that damage plants by eating, in crops of ornamental plants and productive plants, particularly in cotton crops (for example against *Spodoptera littoralis* and *Heliothis virescens*), and in vegetable crops (for example against *Leptinotarsa decemlineata* and *Myzus persicae*).

It is to be emphasised in this connection that the stated compounds are characterised both by a strongly marked systemic as well as contact action against sucking insects, especially against sucking insects of the order Homoptera, and particularly against insects of the Aphididae family (for example *Aphis fabae, Aphis craccivora* and *Myzus persicae*), which are very difficult to control by hitherto known means. Active substances of the formula I exhibit also a favourable action against flies, such as *Musca domestica*, and against mosquito larvae. The compounds of the formula I are in addition characterised by a broad ovicidal and ovilarvicidal action. Furthermore, the compounds of the formula I have a valuable action against phytoparasitic nematodes, as well as against ectoprasitic mites and ticks, for example of the families: Ixodidae, Argasidae and Dermanyssidae.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, broken brick sepiolite or bentonite; and suitable nonsorbent carriers are materials such as calcite or sand. A large number of pre-granulated materials of inorganic or organic nature can also be used, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$-$C_{22}$), for example the sodium or potassium salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkyarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi(2-chloroethyl)ethylammonium bromide.

The tensides customarily used in formulation practice are described, inter alia, in the following publication:

"Mc Cutcheon's Detergents and Emulsifiers Annual", MC Publishing Corp., Ringwood, N.J., 1979.

The pesticidal preparations contain as a rule 0.1 to 99%, particularly 0.1 to 95%, of active substance of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

Formulation examples for liquid active substances of the formula I (%=percent by weight)

| 1. Emulsion concentrates | (a) | (b) | (c) |
|---|---|---|---|
| active substance | 20% | 40% | 50% |
| calcium dodecylbenzenesulfonate | 5% | 8% | 5.8% |
| castor-oil-polyethylene glycol ether (36 moles of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| 2. Solutions | (a) | (b) | (c) | (d) |
|---|---|---|---|---|
| active substance | 80% | 10% | 5% | 90% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active substance | 5% | 10% |
| kaolin | 94% | — |
| highly dispersed silicic acid | 1% | — |
| attapulgite | — | 90% |

The active substance is dissolved in methylene chloride, the solutions is sprayed onto the carrier, and the solvent is subsequently evaporated off in vacuo.

| 4. Dusts | (a) | (b) |
|---|---|---|
| active substance | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I (%=percent by weight)

| 5. Wettable powders | (a) | (b) |
|---|---|---|
| active substance | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active substance is well mixed with the additives and the mixture is thoroughly ground in a suitable mill. Wettable powders which can be diluted with water to give suspensions of the required concentration are obtained.

| 6. Emulsion concentrate | |
|---|---|
| active substance | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active substance | 5% | 8% |
| talcum | 95% | — |
| kaolin | — | 92% |

Dusts ready for use are obtained by mixing the active substance with the carrier and grinding the mixture in a suitable mill.

| 8. Extruder granulates | |
|---|---|
| active substance | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 9. Coated granulate | |
|---|---|
| active substance | 3% |
| polyethylene glycol (M G 200) | 3% |
| kaolin | 94% |

The finely ground active substance is evenly applied, in a mixer, to the kaolin moistened with polyethylene glycol. Dustfree coated granulates are obtained in this manner.

| 10. Suspension concentrate | |
|---|---|
| active substance | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance is intimately mixed with the additives. There is thus obtained a suspension concentrate from which can be prepared, by dilution with water, suspensions of the concentration required.

EXAMPLE 1

Production of the compound of the formula

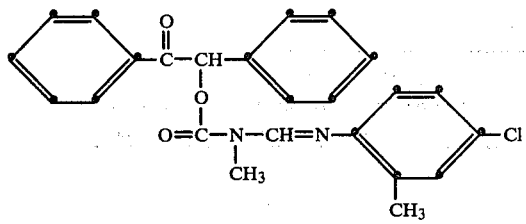

(a) 793.5 g of a 20% solution of phosgene in toluene are added dropwise to a suspension of 227.1 g of benzoin in 250 ml of toluene, and there are subsequently added dropwise at 0° C., within one hour, 168.5 g of N,N-dimethylaniline. The suspension is stirred at 0° C. for 12 hours, and 214 ml of 1 N hydrochloric acid are then added at 0° C. The organic phase is separated in a separating funnel, washed with distilled water and dried with sodium sulfate. The solution thus obtained is added dropwise at 0° C., with stirring, to a suspension of 182.6 g of N'-(4-chloro-2-methylphenyl)-N-methyl-formamidine and 111 g of triethylamine in 600 ml of toluene; and after 2 hours at 0° C. and 12 hours at 20° C., the hydrochloride which has precipitated is filtered off. After removal of the solvent by evaporation, the crude product is dissolved in cyclohexane, and is subsequently freed from residual hydrochloride and unreacted starting products by filtration through a 20 cm silica gel column to thus yield the title compound having a melting point of 53°-56° C.

(b) 100 g of a 20% solution of phosgene in toluene are added dropwise to a suspension of 36.6 g of N'-(4-chloro-2-methylphenyl)-N-methylformamidine in 100 ml of toluene, and there are subsequently added dropwise at 0° C., within one hour, 20.2 ml of triethylamine. The suspension is stirred for 12 hours at 0° C., and 50 ml of 1 N hydrochloric acid are then added at 0° C. The organic phase is washed with distilled water and dried with sodium sulfate. The solution obtained is added dropwise at 0° C., with stirring, to a suspension of 42.5 g of benzoin and 27.8 ml of triethylamine in 150 ml of toluene. After 2 hours at 0° C. and 12 hours at 20° C., the hydrochloride which has precipitated is filtered off. After removal of the solvent by evaporation, the crude product is dissolved in cyclohexane; and is subsequently freed from the residual hydrochloride and unreacted starting products by filtration through a 20 cm silica gel column to thus obtain the title compound having a melting point of 53°-58° C.

The following compounds are produced in an analogous manner:

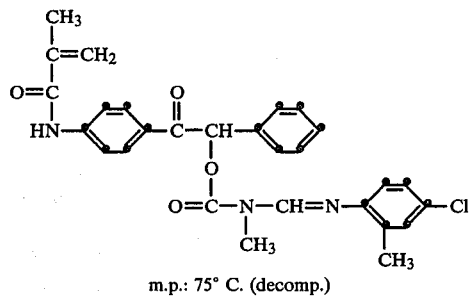

m.p.: 75° C. (decomp.)

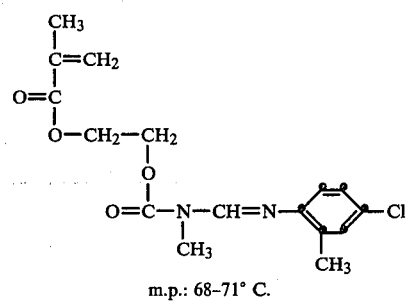

m.p.: 68-71° C.

EXAMPLE 2

Insecticidal stomach-poison action: *Spodoptera littoralis* and *Heliothis verescens*

Cotton plants were sprayed with test solutions containing 50, 100, 200 and 400 ppm, respectively, of the compound to be tested. After the drying of the coating, larvae of the species *Spodoptera littoralis* (L3 stage) and *Heliothis virescens* (L3 stage), respectively, were settled onto the plants. Two plants were used per test compound and per test species, and an evaluation of the attained mortality rate was made after 2, 4, 24 and 48 hours. The test was carried out at 24° C. with 60% relative humidity.

The compounds according to the Production Example exhibited against larvae of the species *Spodoptera littoralis* and *Heliothis virescens* the activity shown in the following Table.

EXAMPLE 3

Action against acarids which damage plants: *Tetranychus urticae (OP-sensitive) and Tetranychus cinnabarinus* (OP-tolerant)

The primary leaves of *Phaseolus vulgaris* plants were infected, 16 hours before the test for acaricidal action, with an infested piece of leaf from a mass culture of *Tetranychus urticae* (OP-sensitive) and *Tetranychus cinnabarinus* (OP-tolerant), respectively [tolerance is with respect to diazinon compatibility]. The plants treated in this manner were sprayed dripping wet with a test solution containing 400 and 200 ppm, respectively, of the compound to be tested. After 24 hours and again after 7 days, an assessment was made, by examination under a binocular microscope of the imagines and larvae (all mobile stages), of living and of dead individuals. One plant was used per concentration and per test species. The plants stood during the course of the test in greenhouse compartments at 25° C.

The compounds according to the Production Example exhibited against individuals of the species *Tetranychus urticae* and *Tetranychus cinnabarinus* the level of activity shown in the following Table.

Biological test results

In the Table which follows are summarised test results based on the Examples given in the foregoing, the index of values with regard to the percentage mortality rate of the parts being as follows:

A: 70–100% mortality with 50 ppm of active substance,
B: 70–100% mortality with 100 ppm of active substance,
C: 70–100% mortality with 200 ppm of active substance, and
D: 70–100% mortality with 400 ppm of active substance.

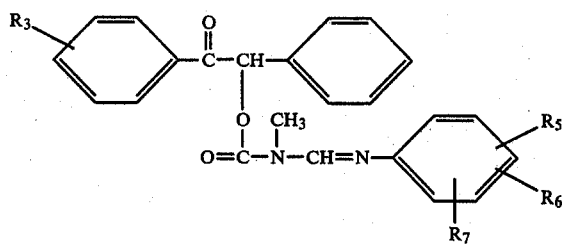

wherein
R$_3$ is hydrogen, acryloyloxy, methacryloyloxy, acrylamido or methacrylamido; and
each of R$_5$, R$_6$, and R$_7$, independently of the others, is hydrogen, halo or alkyl of 1 to 4 carbon atoms.

2. A compound according to claim 1 wherein
R$_3$ is hydrogen or methacrylamido;
R$_5$ is hydrogen, chloro or bromo; and
each of R$_6$ and R$_7$, independently of the others, is hydrogen, chloro, bromo or methyl.

| | Activity against | | | |
|---|---|---|---|---|
| | *Spodoptera littoralis* L$_3$ larvae | *Heliothis virescens* L$_3$ larvae | *Tetranychus urticae* | *Tetranychus cinnabarinus* |
| (structure 1) | B | A | C | C |
| (structure 2) | A | A | C | C |
| (structure 3) | B | B | C | D |

What is claimed is:
1. A compound of the formula:

3. The compound according to claim 1 of the formula

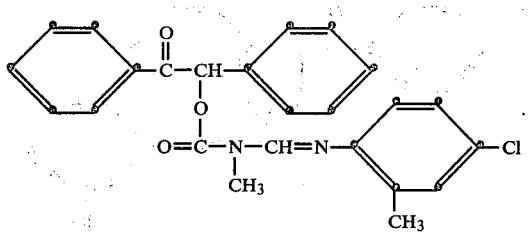

4. The compound according to claim 1 of the formula

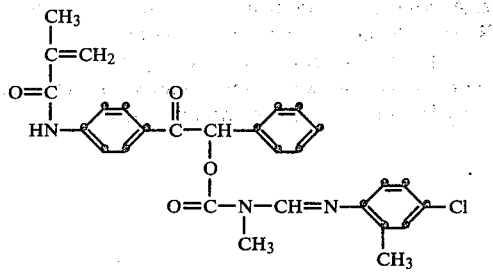

5. A pesticidal composition which contains as active ingredient a compound according to claim 1.

6. A method of combating pests on animals and plants, which method comprises applying thereto or to the locus thereof an effective amount of a compound according to claim 1.

7. A method according to claim 6 for combating insects, and members of the order Acarina.

8. A compound of the formula:

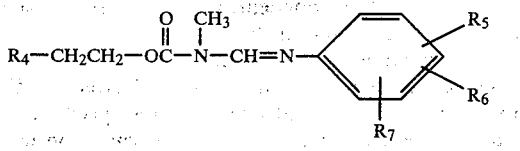

wherein
$R_4$ is acryloyloxy, methacryloyloxy, acrylamido or methacrylamido; and
each of $R_5$, $R_6$ and $R_7$, independently of the others, is hydrogen, halo or alkyl of 1 to 4 carbon atoms.

9. A compound according to claim 8 wherein
$R_4$ is methacryloyloxy;
$R_5$ is methyl, chloro or bromo; and
each of $R_6$ and $R_7$, independently of the others, is hydrogen, chloro, bromo or methyl.

10. The compound according to claim 8 of the formula

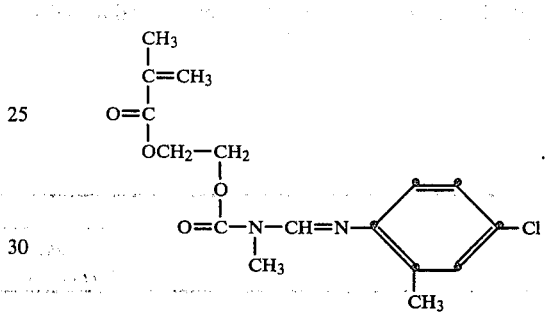

11. A pesticidal composition which contains as active ingredient a compound according to claim 8.

12. A method of combating pests on animals and plants, which method comprises applying thereto or to the locus thereof an effective amount of a compound according to claim 8.

13. A method according to claim 12 for combating insects, and members of the order Acarina.

* * * * *